US005770769A

United States Patent [19]
Geiger et al.

[11] Patent Number: 5,770,769
[45] Date of Patent: Jun. 23, 1998

[54] PROCESS FOR THE PREPARATION OF D,L-METHIONINE OR THE SALT THEREOF

[75] Inventors: Friedhelm Geiger, Erlensee, Germany; Baudouin Halsberghe, Mobile, Ala.; Hans-Joachim Hasselbach, Gelnhausen, Germany; Klaus Hentschel, Rodenbach, Germany; Klaus Huthmacher, Gelnhausen, Germany; Martin Körfer, Johannesberg, Germany; Sven-Peter Mannsfeld, Mobile, Ala.; Herbert Tanner, Hanau; Ferdinand Theissen, Bornheim, both of Germany; Jose Vanrobaeys; Klaus Willigerodt, both of Mobile, Ala.

[73] Assignee: Degussa Aktiengesellschaft, Frankfurt, Germany

[21] Appl. No.: 768,624

[22] Filed: Dec. 18, 1996

[30] Foreign Application Priority Data

Dec. 18, 1995 [DE] Germany .................... 195 47 236.5

[51] Int. Cl.⁶ .............................................. C07C 321/00
[52] U.S. Cl. ............................................... 562/559
[58] Field of Search ...................................... 562/559

[56] References Cited

U.S. PATENT DOCUMENTS

| | | | |
|---|---|---|---|
| 2,557,920 | 6/1951 | White | 260/319 |
| 2,642,459 | 6/1953 | White | 260/534 |
| 3,636,098 | 1/1972 | Takesaburo | 260/534 |
| 3,833,651 | 9/1974 | Ouchi | 260/534 |
| 4,069,251 | 1/1978 | Mannsfeld | 260/534 |
| 4,459,423 | 7/1984 | Doya | 562/559 |
| 4,518,801 | 5/1985 | Bolze | 562/559 |

FOREIGN PATENT DOCUMENTS

| | | |
|---|---|---|
| 0143218 | 6/1985 | European Pat. Off. . |
| 1906405 | 12/1970 | Germany . |
| 1620332 | 4/1972 | Germany . |
| 48014618 | 2/1973 | Japan . |
| 48014619 | 2/1973 | Japan . |
| 50-106901 | 2/1975 | Japan . |
| 50-157318 | 12/1975 | Japan . |
| 03095145 | 4/1991 | Japan . |
| 03095146 | 4/1991 | Japan . |
| 04169570 | 6/1992 | Japan . |
| 7311018 | 2/1974 | Netherlands . |
| 1108926 | 4/1968 | United Kingdom . |
| 1186538 | 4/1970 | United Kingdom . |

OTHER PUBLICATIONS

Terasawa "Preparation of Methionine" Chemical Abstracts, vol. 120, No. 13, Mar. 28, 1994, Abstract 164902t.
Takagi "Alpha–Amino Acids" Chemical Abstracts, vol. 84, No. 7, Feb. 1976, Abstract 44666k.
Kojima "DL–Methionine Alkali" Chemical Abstracts, vol. 85, No. 7, Aug. 1986, Abstract 47049t.
Database WPI, Section Ch. Week 9122–1991 (91–159964).
Database WPI, Section Ch. 1973 (73–64461 U).
Mizuno "Preparation of Methionine" Chemical Abstracts, vol. 117, 1992, Abstract 172112p.
Database WPI, Section Ch. 1973 (73–64461U).
Database WPI, Section Ch. 1972 (73–64462U).

*Primary Examiner*—Michael L. Shippen
*Attorney, Agent, or Firm*—Cushman Darby & Cushman Intellectual Property Group of Pillsbury Madison & Sutro LLP

[57] ABSTRACT

A process for the preparation of methionine or a salt of methionine by reaction of the components 3-methylmercaptopropionaldhyde, hydrogen cyanide, ammonia and carbon dioxide or components from which the above-mentioned components can be prepared, optionally in the presence of water, to 5-(2-methylmercaptoethyl)-hydantoin and further reaction thereof to methionine or the salt thereof, characterised in that the reaction of the components is initiated by means of at least one premixture in such a way that a first mixture is formed containing at least the predominant proportion (at least $5/10$) of the 3-methylmercaptopropionaldeyde and at least $1/10$ of the hydrogen cyanide component or corresponding quantities of components from which these components can be prepared, and less than $5/10$ of one of the components ammonia, carbon dioxide or of the components from which ammonia or carbon dioxide can be prepared, and in that this first mixture is combined with the other component(s) for the reactive conversion to 5-(2-methylmercaptoethyl)-hydantoin, wherein this (these) latter component(s) may be premixed in one or more other mixtures.

31 Claims, 3 Drawing Sheets

PROCESS FOR THE PREPARATION OF D,L-METHIONINE OR THE SALT THEREOF

CROSS-REFERENCE TO RELATED APPLICATIONS

This application is based on DE 195 47236.5 filed on Dec. 18, 1995 in Germany, the entire content of which is hereby incorporated by reference.

BACKGROUND OF THE INVENTION

1. Field of the Invention

The invention relates to a process for the preparation of D,L-methionine or a salt of D,L-methionine, starting from the components 3-methylmercaptopropionaldehyde, hydrogen cyanide, ammonia and carbon dioxide or 5-(2-methylmercaptoethyl)-hydantoin or a salt of methionine or those components from which the above-mentioned components can be prepared, optionally in the presence of water.

The synthesis steps can be illustrated by the following reaction equations:

5-(2-methylmercaptoethyl)-hydantoin formation:

Formation of the salt of D,L-methionine:

Liberation of D,L-methionine:

M stands for alkali metal, alkaline earth metal, ammonium, particularly potassium.

Advantageously, the process steps of 5-(2-methylmercaptoethyl)-hydantoin formation, methioninate formation and methionine liberation may be carried out continuously, advantageously in successive stages which are integrated in a process which, as a whole, takes place continuously, in particular.

Particularly advantageously, the components ammonia and carbon dioxide are recycled in accordance with the process possibilities, i.e. used again in the preceding process stages. Particularly when potassium is used, all the agents containing alkali metal are recycled to the process, if possible.

2. Background Information

The formation of 5-(2-methylmercaptoethyl)-hydantoin is known in principle. Generally speaking, the starting materials are either the components described under 1) or components from which these components can be prepared. These are, in particular, alkali metal- or ammonium salts in the case of the components hydrogen cyanide, ammonia and carbon dioxide, and acrolein and methyl mercaptan in the case of the 3-methylmercaptopropionaldehyde component, as described further below. Chem. Rev. 46 (1959) 422–425 describes the preparation of substituted hydantoins by reaction of the corresponding aldehydes and ketones with alkali metal cyanides and ammonium carbonate. The reaction is carried out either using stoichiometric proportions of the substances at 80° C. and 3 bar or using several times the stoichiometric proportion of ammonia at temperatures up to 60° C. and at normal pressure (DT-PS 11 66 201). It is also known to prepare 5-(2-methylmercaptoethyl)-hydantoin from 3-methylmercaptopropionaldeyde, ammonium carbonate and cyanides. The reaction is carried out initially at 40°–120° C., the reaction mixture is then adjusted to a pH below 4 and the reaction is ended at 50°–100° C. (U.S. Pat. No. 2,557,913). Moreover, it is known to prepare 5-(2-methylmercaptoethyl)-hydantoin by providing a solution which was prepared by dissolving 3-methylmercaptopropionaldehyde in an aqueous solution of ammonia, carbon dioxide and hydrocyanic acid or the salts thereof and in which, optionally, a reaction to hydantoin has taken place partially or wholly, and introducing into this solution an aqueous solution of ammonia, carbon dioxide and hydrocyanic acid or the salts thereof and, separately, the 3-methylmercaptopropionaldehyde, and carrying out the reaction by heating the mixture to a temperature up to 100° C. at normal pressure (DT-OS 16 20 332). In Japanese patent JP 48-005763, 3-methylmercaptopropionaldehyde is reacted with hydrogen cyanide or the salts thereof and ammonium carbonate in the presence of ammonia and at 80° C. in 1.5 hours to form 5-(2-methylmercaptoethyl)-hydantoin in a 98.5% yield. Added metal ion complexing agents in the presence of water lead to a 97.8% yield (JP 48-004465). A similar reaction in the presence of organic solvents at 50°–200° C. under pressure in the liquid phase is described in patent JP 40-36676. A one-pot variant starting from acrolein, methylmercaptan, hydrogen cyanide and ammonium carbonate in water at 50°–70° C. leads within 2 hours to a hydantoin which is saponified to D,L-methionine (JP 50-004018).

The reaction described in JP 52-027768 takes place in a similar manner, but with the addition of amino acids such as methionine, threonine, glycine, alanine, or leucine. 3-Methylmercaptopropionaldehyde, carbon dioxide, ammonia, hydrogen cyanide and caustic alkali at 80° C. lead to 97% 5-(2-methylmercaptoethyl)-hydantoin within 2 hours (JP 50-018467).

3-Methylmercaptopropionaldehyde, sodium cyanide and ammonium carbonate in water in the presence of potassium thiosulphate or potassium carbonate give 5-(2-methylmercaptoethyl)-hydantoin (SU 740770). In the single-stage reaction of acrolein with methyl mercaptan, hydrogen cyanide and ammonium carbonate, 5-(2-methylmercaptoethyl)-hydantoin is produced in an 85% yield (Asahi Chem. Ind., Agric. Biol. Chem. 52, 589 (1988). The Chinese patent CN 85 1085905 also describes a single-stage reaction, but with the addition of methionine in acetic acid with 91% conversion to 5-(2-methylmercaptoethyl)-hydantoin.

A 5-(2-methylmercaptoethyl)-hydantoin prepared by the known methods is contaminated to a considerable extent by 5-(2-methylmercaptoethyl)-hydantoic acid, 5-(2-methylmercaptoethyl)-hydantoic acid amide, methioninamide, methionine nitrile and methylmercaptopropionaldehyde cyanohydrin, iminonitrile and polymers. Whilst the first three compounds mentioned, like the hydantoin, are converted to methionine during alkaline hydrolysis, the other compounds or the saponification products thereof enter the saponification solution and the methionine to be isolated later, where they can be separated only with great difficulty. This is particularly so when the methionine is prepared from the hydantoin and separated from the reaction mixture using carbon dioxide and the mother liquor recycled. The methionine obtained is discoloured and has poor storage stability.

Alkaline hydrolysis of 5-(2-methylmercaptoethyl) hydantoin is by no means new. U.S. Pat. No. 2,527,366 and U.S. Pat. No. 2,557,913 describe the hydrolysis of 5-(2-methylmercaptoethyl)-hydantoin in an aqueous barium hydroxide solution under pressure and at elevated temperature. These processes require substantial quantities of expensive barium hydroxide, however; moreover, the barium has to be separated again as a neutral salt.

It is known from U.S. Pat. No. 2,557,920 that α-amino acids are produced by saponification of hydantoins using sodium hydroxide. In these processes, however, at least 3 moles of sodium hydroxide per mole of hydantoin are required. The situation is similar when potassium hydroxide is used.

Moreover, it is known from U.S. Pat. No. 4,272,631 that a mixture of alkali metal and alkaline earth metal hydroxide may be used to saponify 5-(2-methylmercaptoethyl)-hydantoin. In these processes, however, the alkaline earth metal ions first have to be separated during the liberation of methionine, so maximum yields of only 80.5% are obtained.

In U.S. Pat. No. 4,259,925, the hydrolysis of 5-(2-methylmercaptoethyl)-hydantoin is carried out under pressure at 105° to 230° C. in a medium that contains a metal hydroxide and an alcohol with a boiling point of 125° to 130° C. A disadvantage is that the high-boiling alcohol has to be recovered. Moreover, the yield is only 65%.

The hydrolysis of 5-(2-methylmercaptoethyl)-hydantoin using an aqueous solution of alkali carbonate and/or alkali hydrogen carbonate is described in DE-PS 19 06 405. Ammonia and carbon dioxide are removed continuously during hydrolysis. The preferred alkali metal carbonate is potassium carbonate; a molar ratio of hydantoin to alkali metal of 1:1 to 1:5 is used. Hydrolysis is carried out under pressure at 120° to 220° C. The continuous pressure apparatus is composed of three rotary evaporators set up at great expense in series. The alkali metal methioninate solution is used to liberate D,L-methionine with carbon dioxide; the mother liquor obtained from the separation of the methionine that crystallises out is recycled, optionally with the removal of 1–2%, and used again for the hydrolysis of hydantoin.

DE-AS 15 18 339 describes a process in which gaseous reaction products (ammonia and carbon dioxide) produced during hydrolysis are removed from the reaction in order to shift the reaction equilibrium towards the amino acid, as a result of which the yield is increased. In order to achieve this, however, a complex arrangement of apparatus is required to regulate the pressure of the gas streams.

Japanese patent 49/116 008 describes a process in which the hydrolysis of 5-(2-methylmercaptoethyl)-hydantoin is carried out in the presence of vanadic acids, molybdic acids, tungstic acids or the derivatives thereof. The yields are about 70%. The separation of the catalyst is difficult. In order to prepare a highly concentrated methionine-containing solution, alkali metal e.g. a potassium compound, must be added.

It is known from the Japanese patent application 75/106 901 (C.A. 84,44666k (1976)) that methionine is prepared by hydrolysis of 5-(2-methylmercaptoethyl)hydantoin in the presence of about 1.2 equ. of sodium hydroxide and about 9 equ. of ammonia at 180° C. The sodium methioninate solution obtained as an intermediate with this mode of operation necessarily contains not only sodium methioninate, however, but also sodium carbonate which precipitates whilst this reaction is being carried out and is therefore troublesome, particularly in a continuous process. The same is true of the use of potassium hydroxide and of the method of operating according to DE-PS 19 06 405.

DE 26 14 411 A describes the hydrolysis of 5-(2-methylmercaptoethyl)-hydantoin with water in the presence of imidazole at 160° C. The yields are low and here, too, an alkali metal compound has to be added in order to obtain a high solution concentration.

Japanese patent applications JP 03/95145 and JP 03/95146 describe the hydrolysis of hydantoins with water at elevated temperature and elevated pressure in the presence of metal oxides or oxide mixtures, for example $ZrO_2$, $TiO_2$, $Nb_2O_5$ or $TiO_2$—$Nb_2O_5$; the yields are only 65 to 66%, however. These solutions must be neutralised with an alkali compound.

All these processes bring either low yields or have the disadvantage that methionine or salts such as carbonates are precipitated during the process, as a result of which further process steps are brought about and industrial-scale processes in particular, more particularly continuous processes, are scarcely possible.

The liberation of methionine from the alkali metal salt is generally known. According to the principle that strong acids liberate weaker acids from their salts, free D,L-methionine is precipitated e.g. with hydrochloric acid, sulphuric acid, phosphoric acid or a strongly acid ion exchanger (DE 21 40 506 C; DE 21 22 491 C; DE 29 12 066 A; BE 877 200, U.S. Pat. No. 3,433,832, FR 1 532 723). The alkali metal salt obtained as a by-product must then, however, be separated. As the acid used is not generally recovered, this method of operating is unsuitable for a continuous economic and environmentally acceptable production process.

As described for example in the patents U.S. Pat. No. 2,557,913, DE-PS 19 06 405 and JP 42/44056, D,L-methionine was therefore precipitated advantageously from the hydrolysis solutions of 5-(2-methylmercaptoethyl)-hydantoin with carbon dioxide in aqueous solution. In this method, D,L-methionine is usually obtained in the form of thin leaves or as flakes. This causes the product to be difficult to filter and prevents the crystal cake being washed out; moreover, a D,L-methionine with poor flow properties and a tendency to form lumps is obtained. In order to counter these disadvantages, according to Japanese patent JP 42/44056, additives such as casein or water-soluble, high molecular weight cellulose derivatives are added during the precipitation of methionine with carbon dioxide.

SUMMARY OF THE INVENTION

The object of the present invention is a process for the preparation of methionine or a salt of methionine in which as few by-products as possible are produced and the individual components of which can be separated easily; in particular, when a product is precipitated, it should be easy to filter. It should be possible to recycle or regenerate individual components to a large extent. Moreover, the methionine obtained should have little discoloration and should be stable in storage. It should be possible to carry out the process on an industrial scale in particular, and continuously.

According to the invention, this object is achieved with a process for the preparation of methionine or a salt of methionine by reaction of the components 3-methylmercaptopropionaldehyde, hydrogen cyanide, ammonia and carbon dioxide or those components from which the above-mentioned components can be prepared, optionally in the presence of water, to 5-(2-methylmercaptoethyl)-hydantoin and further reaction thereof to methionine or the salt thereof, wherein the reaction of the components is initiated by means of at least one premixture in such a way that a first mixture is formed containing at least the predominant proportion (at least $5/10$) of the 3-methylmercaptopropionaldehyde and at least $1/10$ of the hydrogen cyanide component or corresponding quantities of components from which these components can be prepared, and less than $5/10$ of one of the components ammonia, carbon dioxide or of the components from which ammonia or carbon dioxide can be prepared, and that this first mixture is combined with the other component(s) for the reactive conversion to 5-(2-methylmercaptoethyl)-hydantoin, wherein this (these) latter component(s) may be premixed in one or more other mixtures.

Components from which the above-mentioned components can be prepared include, for example, salts of hydrogen cyanide, ammonia and carbon dioxide, for example sodium- or potassium cyanide, ammonium carbonate or bicarbonate, sodium or potassium carbonate or bicarbonate and, of course, in particular the solutions thereof in water. Corresponding components for 3-methylmercaptopropionaldehyde are acrolein and methyl mercaptan. In principle, it is preferable to use any metal salts used in this reaction in less than stoichiometric quantities, i.e. the aldehyde component and/or the cyanide component is in stoichiometric excess to any metal ion component used. Particularly preferably, no metal salt e.g. sodium or potassium cyanide is used here if possible, the above-mentioned compounds being used in preference. In a continuous process in particular, however, other metal salts may be present in addition, e.g. catalysts or the like. The metered quantity thereof does not come under the preferred metal ion restriction given above as regards the reaction components.

In this context and hereinafter the stated components are also taken to mean their altered form of use under the given conditions of use. For example, when ammonia and carbon dioxide are used in water, a part of these components is present as ammonium (hydrogen) carbonate.

According to this process, the 5-(2-methylmercaptoethyl)-hydantoin is obtained as a colourless product in a practically quantitative yield and is free to such a large extent from impurities that a methionine or the salt thereof may be obtained from it in a continuous process with mother liquor recycling and is characterised by extraordinary storage stability in terms of discoloration and lump formation.

Preferably, the first mixture contains at least $5/10$ of the hydrogen cyanide component, particularly $9/10$ and particularly at least $99/100$ or corresponding proportions of the component from which hydrogen cyanide can be prepared. The fractions above (e.g. $5/10$) and hereinafter always relate to the stated component itself (not to the stoichiometry of the process). Irrespective of the stoichiometry, therefore, the total quantity of a component used is $1/1$.

In particular, it is advantageous in the process if ammonia and carbon dioxide or those components from which ammonia or carbon dioxide can be prepared are each used in the first mixture in quantities of less than $5/10$ or their use quantities, preferably at most $1/10$ and in particular at most $1/100$.

It is also advantageous if the water optionally added to the reaction is contained in the first mixture in a quantity of at most $5/10$, preferably at most $1/10$ and in particular at most $1/100$.

It is also advantageous if, at the beginning of the reaction, all the components are present in their entirety in their intended use quantity, i.e. that no component is metered in afterwards. It is also advantageous if all the components are combined in a total of two premixtures which are then mixed together for the reaction.

In all the reactions it is particularly favourable if the individual components or premixtures are mixed together rapidly and, if possible, intimately.

The reaction mixture preferably contains no organic solvents but if organic solvents are used then their quantity is advantageously less than 20 parts by weight, particularly less than 10 parts by weight, based on 100 wt. % of water.

It is particularly advantageous if the premixture(s) and optionally individual components (one or more premixtures may be caused to react; in the case of two premixtures, optionally all the individual components may be contained therein) are introduced into a reaction mixture already obtained and containing 5-(2-methyl-mercaptoethyl)-hydantoin. It is particularly advantageous in this case if all the premixture(s) and optionally individual components are introduced into the reaction mixture either adjacently or at staggered intervals (in the case of batchwise preparation) or flow-dependent intervals (in the case of continuous preparation) of at most 30 s.

The reaction in the method of operating described above is carried out preferably at a temperature above 80° C.; moreover, the reaction is carried out preferably at a pressure above atmospheric, particularly preferably at a pressure greater than the equilibrium pressure carried (reaction pressure), particularly at a pressure of at least 3 bar and particularly preferably above 10 bar.

The process described above with its variants is particularly suitable for continuous operation.

In a process for the preparation of methionine or a salt of methionine, in particular two of the process measures described above are by themselves particularly advantageous, so the invention also relates to a process for the continuous preparation of methionine or a salt of methionine, with the reaction of the components 3-methylmercaptopropionaldehyde, hydrogen cyanide, ammonia and carbon dioxide or of those components from which the above-mentioned components can be prepared, optionally in the presence of water, to 5-(2-methylmercaptoethyl)-hydantoin and further reaction thereof to methionine or the salt thereof, wherein the components are introduced into a reaction mixture which is formed from the above-mentioned components and already contains at least $1/10$ of the quantity of 5-(2-methylmercaptoethyl)-hydantoin that can theoretically be formed, and wherein the reaction is carried out at a pressure above atmospheric, preferably at a pressure of at least 3 bar.

It is particularly advantageous if operations are carried out at a pressure of at least 7 bar and particularly at a pressure of at least 10 bar. Moreover, it is particularly advantageous if the components are fed into the reaction mixture immediately or with a flow-dependent pre-reaction time of at least 30 s, i.e. if the individual components are in reactive contact for at most 30 s before being introduced into the reaction mixture.

Moreover, the individual advantageous measures described above can also be carried out with this process variant.

The processes described hitherto are carried out particularly preferably as one process, a corresponding summary description of this process being given below. The other specifications given herein, e.g. regarding the stoichiometry, temperatures etc., are also each by themselves applicable advantageously to the processes described in a general manner above.

According to the invention, 5-(2-methylmercaptoethyl)-hydantoin is prepared in a particularly advantageous manner by preparing a solution of hydrogen cyanide in 3-methylmercaptopropionaldehyde and a solution of ammonia and carbon dioxide in water and mixing these solutions rapidly and intimately and causing them to react. Ammonia and carbon dioxide may be returned from the hydrolysis stage of this hydantoin. The solution of hydrogen cyanide in 3-methylmercaptopropionaldehyde is advantageously adjusted such that it comprises equimolar proportions of hydrogen cyanide and 3-methylmercaptopropionaldehyde, or contains excess proportions of hydrogen cyanide. Even so, it is advantageous to select a proportion of hydrogen cyanide in the solution of not more than 1.1 mole per mole of 3-methylmercaptopropionaldehyde; the solution preferably contains 1.005 to 1.05 mole of hydrogen cyanide per mole of 3-methylmercaptopropionaldehyde.

This solution of ammonia and carbon dioxide in water may be a saturated or dilute solution; advantageously, the ammonia content is not less than about 5 wt. %. Ammonium hydrogen carbonate, ammonium carbonate, carbamic acid, ammonium carbamate, cyanic acid or a mixture of these components may be present in the solution. The molar ratio of ammonia to carbon dioxide is advantageously about 1.2 to 4.0 mole, preferably 1.6 to 1.8 mole of ammonia per mole of carbon dioxide. The solution of hydrogen cyanide in 3-methylmercaptopropionaldehyde is mixed with the solution of ammonia and carbon dioxide in water in such a way that a molar ratio of ammonia to 3-methylmercaptopropionaldehyde of about 1.2–6 to 1.0, preferably 2.0–4.0 to 1.0, particularly 2.5–3.0 to 1.0 is advantageously present in the mixture.

The reaction is carried out at ambient temperature or above, advantageously at temperatures above 60° C., advantageously approximately between 80° C. and 140° C. In preference, temperatures between 80° and 130° C., particularly between 90° and 120° C. are selected. Although the reaction may take place at any desired pressure, it is advantageous to operate at elevated pressure; pressures of up to 20 bar have proved advantageous, particularly pressures that are 2 to 3 bar above the equilibrium pressure of the reaction mixture. The reaction time depends on the reaction conditions, particularly on the temperature and quantity ratios.

In the preferred mode of operation, it is particularly advantageous to introduce the solution of hydrogen cyanide in 3-methylmercaptopropionaldehyde and the solution of ammonia and carbon dioxide in water into a reaction mixture of these substances, i.e. into a mixture obtained beforehand during the reaction of the solutions in which the reaction of the hydantoin has taken place wholly or partially, and to carry out the reaction in this mixture.

It is particularly advantageous to select a continuous mode of operation, to recycle the reaction mixture to this end, to feed the solutions of hydrogen cyanide in 3-methylmercaptopropionaldehyde and of ammonia and carbon dioxide in water continuously at two adjacent locations in this circuit and to draw off an appropriate proportion of the reaction mixture continuously from the circuit at another location. Although the mixing ratio between the solutions that are fed into the circuit and the reaction mixture which is recycled may be any ratio, it is advantageous to select this mixing ratio such that several parts by volume of the reaction mixture, optionally 1000 or more, preferably 5 to 100, particularly 10 to 25 parts by volume of the reaction mixture, are present per part by volume of the solutions. It is decidedly advantageous to mix the solutions fed into the circuit with the recycled reaction mixture rapidly and intimately; this may be brought about optionally by means of a mixing nozzle, a static mixer, by means of a high circulation rate, or a combination of all the measures. It is possible that the reaction has not taken place completely in the proportions of the reaction mixture drawn off from the circuit, so it may be advantageous to allow these proportions to finish reacting for a certain period in a secondary reactor. If less than 5 parts by volume of the reaction mixture are present per part by volume of solutions, there is a risk of polymerisation of the starting components. The mixture becomes dark in colour, precipitation occurs and hence losses of yield and/or technical disturbances.

According to the present invention, the 5-(2-methylmercaptoethyl)-hydantoin prepared as described above or by another manner or means may be reacted further to an alkali metal salt of methionine or optionally further to methionine. The invention therefore also relates to a process for the preparation of methionine or an alkali metal salt of methionine by hydrolysis of 5-(2-methylmercaptoethyl)-hydantoin in the presence of an aqueous solution containing alkali metal and carbon dioxide, and optionally further reaction to methionine, wherein hydrolysis is carried out at least at the beginning in the presence of at least 0.1 equ., particularly up to 7 equ. of ammonia per equivalent of 5-(2-methylmercaptoethyl)-hydantoin. The invention also relates to a process for the preparation of an alkali metal salt of methionine by hydrolysis of 5-(2-methylmercaptoethyl)-hydantoin in the presence of an aqueous solution containing alkali metal and carbon dioxide, and optionally further reaction to methionine, wherein hydrolysis is carried out in the presence of metallic zirconium or a zirconium alloy containing at least 10 wt. % of zirconium.

It is particularly advantageous if both processes according to the invention are combined.

It has become apparent that it is particularly advantageous if hydrolysis is carried out from the outset in the presence of metal and carbon dioxide, i.e. if in particular a mixture of alkali metal compounds is present, particularly alkali hydrogen carbonate, alkali carbonate, alkali hydroxide, where alkali stands in particular for potassium and sodium. The quantity of alkali metal and carbon dioxide is advantageously at least the stoichiometric quantity based on the hydantoin. This quantity may be substantially higher than stoichiometric. A molar ratio with an excess of about 3:1 based on the hydantoin is particularly advantageous; in principle, it must be assumed that an even greater excess is even more favourable. For practical purposes, however, ratios of about 1.5:1–2:1 are particularly preferred. According to the invention, a little ammonia is added in addition, this likewise being present accordingly in the form of ammonium compounds. It is particularly advantageous if, at the beginning of hydrolysis, max. 7 moles of ammonia (incl. ammonium compounds) are present per mole of 5-(2-methylmercaptoethyl)-hydantoin. As a result, hydrolysis takes place with practically no by-product formation and in good yields and, on the other hand, little or no alkali metal carbonate precipitates out. It is particularly advantageous if, during hydrolysis, ammonia and/or carbon dioxide, optionally together with water, are removed from the reaction system. The reaction conditions can thereby be controlled in a particularly favourable manner so that no alkali metal carbonate precipitates out and the reaction takes place completely. It is particularly advantageous if the hydrolysis apparatus itself contains zirconium fittings (made of zirconium or a corresponding zirconium alloy). It was ascertained that zirconium has a particularly favourable effect, presumably catalytic, on hydrolysis. A favourable secondary effect is that this apparatus is highly resistant and thus durable, so the use of zirconium apparatus does not bring about any apparatus-dependent disadvantages compared with other apparatus.

The hydrolysis processes are carried out advantageously at a temperature of 120° to 250° C. and, accordingly, at a pressure of 5 to 30 bar. Very good conversions and little by-product formation are obtained in this range. It is also advantageous if the alkali metal component is used at least in an equimolar proportion with regard to 5-(2-methylmercaptoethyl)-hydantoin. In that case, in addition to complete hydrolysis, the corresponding alkali metal salt of methionine is obtained practically quantitatively. In preference, the hydrolysis solution already contains methionine or the salt thereof at the beginning; this, too, has a favourable, presumably autocatalytic effect on hydrolysis.

With this method of operating, practically all the ammonia and all the carbon dioxide may be drawn off from the hydrolysis solution during or after hydrolysis, so the hydrolysate may be removed in a form which is substantially free from ammonia and carbon dioxide.

In this case, too, it is particularly advantageous to carry out the process continuously. It is more particularly advantageous that the processes described hitherto may be coupled together, particularly as a continuous process in which carbon dioxide and ammonia may be recycled.

DETAILED DESCRIPTION OF THE INVENTION

The invention will be described in more detail below with regard to hydantoin hydrolysis; in principle, individual detailed specifications by themselves also apply to the general method of operating given above. The method of operating reproduced below is described for corresponding potassium compounds since this is the most preferred embodiment.

According to the invention, a potassium methioninate solution is obtained by hydrolysis of 5-(2-methylmercaptoethyl)-hydantoin in the presence of potassium hydroxide, potassium carbonate and/or potassium hydrogen carbonate or a mixture thereof and in the presence of excess ammonia, carbon dioxide, carbonic acid, cyanic acid or a mixture thereof in water at a temperature of 120° to 250° C. and a pressure of 5 to 30 bar. Advantageously, hydrolysis of the hydantoin takes place in the presence of 1 to 15 equ. of one or more potassium compounds, based on the hydantoin (e.g. KOH, $KHCO_3$, $K_2CO_3$, potassium methioninate). During or after hydrolysis, it is also advantageous if ammonia produced or still present and/or carbon dioxide is separated wholly or partially from the reaction system. In principle, any 5-(2-methylmercaptoethyl)-hydantoin may be used; advantageously, the hydantoin used is one which may be obtained in the manner described above.

Advantageously, the ammonia is in a molar ratio to carbon dioxide of 1.1 to 8.0 at the beginning of hydrolysis. A molar ratio of ammonia to the hydantoin of 0.2 to 5 is also favourable. In the method of operating described, it is possible to take the ammonia and the carbon dioxide directly from the process described above, hydantoin preparation, so that the hydantoin directly from hydantoin preparation together with any ammonia and carbon dioxide remaining may be introduced into the hydrolysis stage where ammonia and/or carbon dioxide may then be adjusted to different concentrations, if desired.

In the process according to the invention, the hydrolysis of 5-(2-methylmercaptoethyl)-hydantoin takes place at temperatures of 120°–250° C., preferably 150°–200° C., particularly 160°–180° C.; the pressure during the reaction should be 5–30 bar, preferably 5–10 bar, particularly 7–9 bar.

The process is carried out advantageously in a steam-heated column with fittings, in which the internal wall and the fittings are composed of zirconium or of a zirconium alloy containing at least 10 wt. % of zirconium. Advantageously, the 5-(2-methyl-mercaptoethyl)-hydantoin solution is introduced continuously at the top of the column at a rate such that the hydrolysis product, potassium methioninate solution, may be drawn off in a corresponding amount at the bottom, i.e. hydrolysis at the bottom of the column has taken place quantitatively. The gaseous constituents water vapour, ammonia and carbon dioxide are removed advantageously at the top of the column and may be used advantageously to restore the aqueous ammonia/carbon dioxide solution for the preparation of 5-(2-methylmercaptoethyl)-hydantoin.

According to the invention, an aqueous solution of potassium hydroxide, potassium carbonate and/or potassium hydrogen carbonate with a potassium ion content of advantageously 100–200 g, preferably 140–160 g of potassium per litre of hydrolysis solution is used for the hydrolysis of 5-(2-methylmercaptoethyl)-hydantoin, the apparatus walls and fittings composed of zirconium exerting a favourable catalytic effect on hydrolysis, so that this takes place largely without the formation of by-products. Advantageously, in a continuous process, the mother liquor is used again at this juncture after methionine solids separation; the mother liquor may additionally contain residual methionine—according to the solubility—and this has also proved to be advantageous for the process.

The average residence time of the reaction solution in the hydrolysis column is advantageously 10–20 minutes. The molar ratio of the potassium ion quantity to the sum of 5-(2-methylmercaptoethyl)-hydantoin+methionine is favourably up to 10, preferably 1.3–5, particularly 1.5–2. The potassium methioninate yield obtained in the reaction solution is typically 99.0–100% with this method of operating. The potassium methioninate concentration may be adjusted by making an appropriate choice of hydantoin concentration or by diluting or concentrating the solution obtained after hydrolysis.

The present invention also includes the liberation of methionine from alkali metal methioninate, advantageously from an aqueous solution of the kind that may be obtained by the methods of operating above. The invention therefore also relates to a process for the preparation of methionine from metal methioninate in aqueous solution by liberation with carbon dioxide, wherein a defoaming agent is added to the aqueous solution containing alkali metal methioninate before liberation of the methionine. The invention also relates to a process for the preparation of methionine from alkali metal methioninate in aqueous solution by liberation with carbon dioxide, wherein the liberation is carried out in a stirred-cell reactor with intensive mixing or in a stirred reactor with quasi ideal mixing.

These two methods of operating are advantageously combined. All compounds that have a foam-inhibiting function are suitable as defoaming agents. The defoaming agent is introduced into the solution preferably in the form of a dispersion. As a result, a particularly good distribution is obtained in the solution rather than a concentration essentially on the surface of the aqueous solution. The favourable effect of the defoaming agent on the liberation of methionine is thereby promoted, particularly the prevention of the formation of thin leaves or flakes. Solid, spherical crystals are obtained, predominantly with a diameter of 100 to 200 $\mu$m.

The defoaming agent is added advantageously in a concentration of 1,000 to 10,000 ppm, based on the total methionine (methionine+methioninate, converted to methionine).

When methionine is liberated from the aqueous solution by means of carbon dioxide, it is particularly advantageous if the carbon dioxide is fed into the aqueous solution by means of a nozzle device in the region of the bottom. This in turn promotes the liberation of methionine. Moreover, liberation is carried out advantageously at a pressure of 1 to 30 bar, preferably also at a temperature of 0° to 100° C.

An aqueous solution that is essentially free from ammonia is used in particular preference.

The last method of operating is also carried out continuously in particular preference. The method of operating described is advantageously combined with the method of operating described above for the preparation of an alkali metal salt of methionine, the entire combination of the methods of operating described above being possible in particular preference.

The process for the liberation of methionine is described below on the basis of the preferred potassium-D,L-methioninate, although other alkali metals e.g. sodium are also possible. The other preferred or general process conditions given here also apply accordingly to the general method of operating described above.

During the liberation of D,L-methionine from potassium-D,L-methioninate by feeding carbon dioxide particularly into a hydrolysis solution of 5-(2-methylmercaptoethyl)-hydantoin, it is particularly advantageous if the solution is practically free from ammonia. In preference, the solution also contains dissolved D,L-methionine. Certain quantities of potassium carbonate and potassium hydrogen carbonate may also be present. The solution may, if desired, be purified over activated carbon prior to the addition of carbon dioxide. The addition of carbon dioxide usually takes place at a temperature of 0° to 100° C., preferably at 20° to 35° C. and usually at a pressure of 1 to 30 bar, preferably 2 to 5 bar. The carbon dioxide is fed into the reaction mixture preferably until a pH of about 7 to 9, preferably 7.5 to 8.5 is reached and/or until the precipitation of D,L-methionine has ended. It is particularly advantageous if the carbon dioxide is introduced at the bottom of the reactor directly or advantageously in the finely divided form by means of a nozzle device. The reactor advantageously takes the form of a stirred-cell reactor or a quasi ideal stirred reactor. Moreover, particularly in a continuous mode of operation, the defoaming agent may additionally increase the throughput. The defoaming agent is usually added in a quantity of at least 1,000 and advantageously up to 10,000 ppm, preferably 3,000 to 5,000 ppm, based on the total methionine present in the reaction solution, particularly as an aqueous emulsion. The methionine liberated is advantageously separated from the mother liquor and is largely free from dust after drying and characterised by good flow properties and a high bulk density. The methionine particles have a diameter of predominantly 100 to 200 $\mu$m. With this method of operating, the yield of isolated D,L-methionine is usually 98 to 100%. The mother liquor obtained after D,L-methionine separation, particularly filtration, may advantageously be used again for the hydrolysis of 5-(2-methylmercaptoethyl)-hydantoin, optionally after concentration and/or discharge of $CO_2$.

The invention is explained in more detail below on the basis of Figures and Examples.

EXAMPLES 1–4

Examples of the preparation of 5-(2-methylmercaptoethyl)-hydantoin

Figure 1:
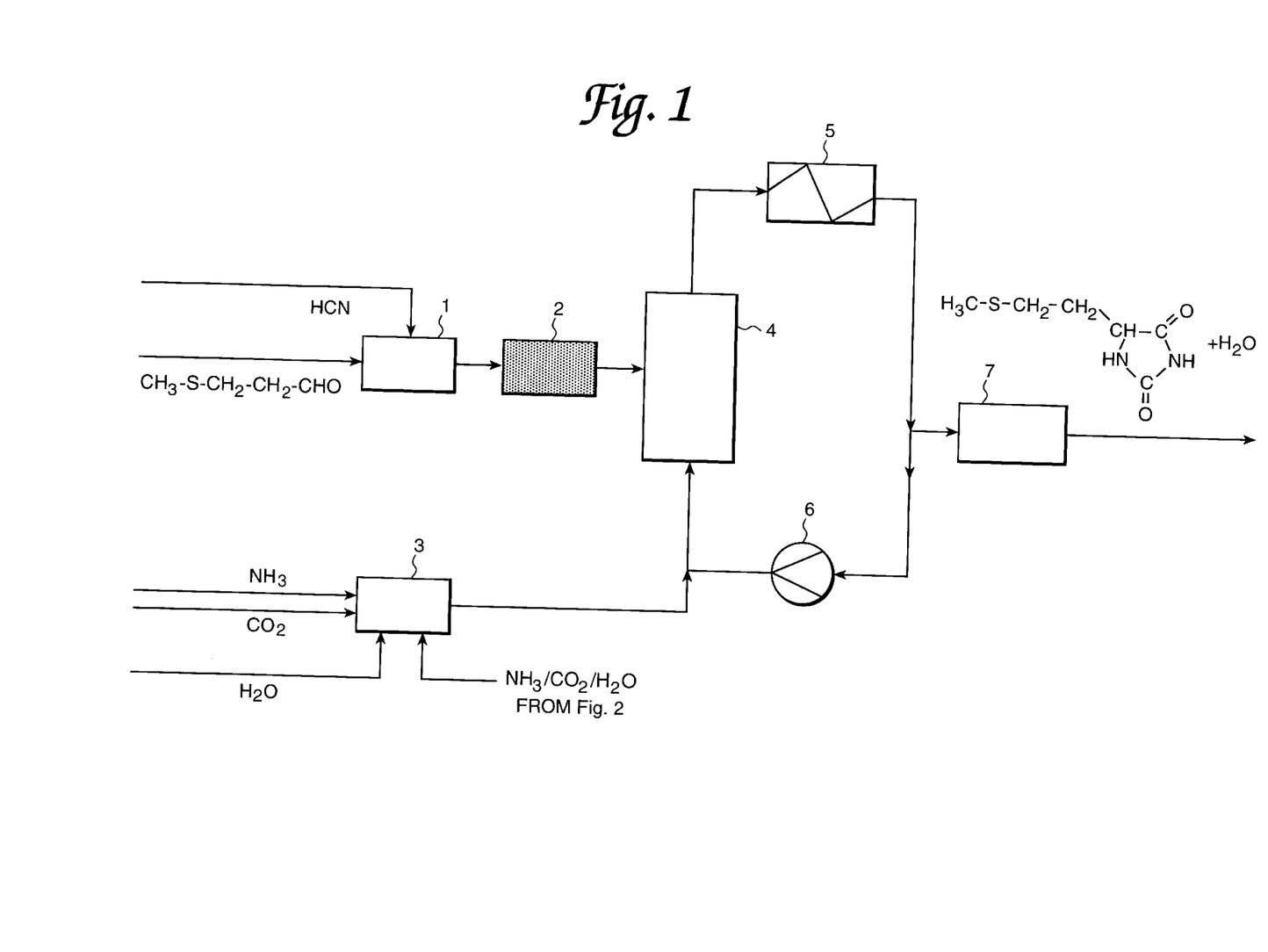
FIG. 1 shows a process sketch of the continuous preparation of 5-(2-methylmercaptoethyl)-hydantoin.

The general process for Examples 1–4 is shown in FIG. 1. In the continuous mode of operation, hydrogen cyanide is mixed by means of a mixing nozzle 1 with 3-methylmercaptopropionaldehyde and a downstream static mixer 2. A solution of ammonia and carbon dioxide in water, which components may be recycled from the subsequent stages, is prepared in a mixing reactor 3. The two mixtures are fed continuously into the reaction mixture in a circulation reactor 20. A good temporary mixing of the solutions with the recycled reaction mixture takes place in a mixing device 4. The circulating mixture is pumped 6 via a heat exchanger 5 with which the desired temperature is adjusted. An appropriate proportion of the reaction mixture is drawn off continuously from the circuit. This proportion is then fed to a secondary reactor 7 to complete the reaction. The product mixture thus obtained may then be conveyed, optionally immediately, to the next reaction stage.

Example 1

A device as in FIG. 1 was used. Initially, water heated to 90° C. was circulated; a solution of 10.5 mole of hydrogen cyanide in 10 mole of 3-methylmercapto-propionaldehyde and 6.8 1 of an aqueous ammonium carbonate solution containing 9.6 wt. % of ammonia and 15.2 wt. % of carbon dioxide was then fed hourly into the circuit. The circulation in the circuit was 300 l per hour. The temperature was kept at 90° C.; the pressure was 14 bar. A volume of reaction mixture corresponding to the inflow was drawn off constantly from the circuit and fed to the secondary reaction. The average residence time was 10 min in the circuit and 2 h in the secondary reaction. The yield of 5-(2-methylmercaptoethyl)-hydantoin or of compounds saponifiable to methionine, based on 3-methylmercaptopropionaldehyde used, was 99.8%. (The details are based on 3-methylmercaptopropionaldehyde, calculated as 100%).

Example 2

The procedure was the same as in Example 1 but an ammonium carbonate solution saturated at room temperature and containing 9.6 wt. % of ammonia and 15.2 wt. % of carbon dioxide was circulated at the beginning instead of water. The yield was 99.7%.

Example 3

The procedure was the same as in Example 1, but the temperature in the circuit and during the secondary reaction was kept at 115° C. The pressure was 16 bar. The circulation in the circuit was 150 l per hour. The average residence time was 6 min in the circuit and 20 min in the secondary reaction. The yield obtained was 99.9%.

Example 4

The procedure was the same as in Example 1 but a solution of 10.1 mole of hydrogen cyanide in 10.0 mole of 3-methylmercaptopropionaldehyde and 6.8 l of an aqueous ammonium carbonate solution containing 5.5 wt. % of ammonia and 8.5 wt. % of carbon dioxide was fed in hourly. The temperature in the circuit and during the post-reaction was kept at 115° C. The pressure was 16 bar. The flow rate in the circuit was 150 l per hour; the average residence time was 6 min in the circuit and 40 min in the secondary reaction. The yield was 99.8%.

Examples 5 and 6

Examples of the preparation of potassium methioninate solution

The general process for the preparation of potassium methioninate solution is reproduced in FIG. 1.

Example 5

Comparison example with a pressure apparatus without zirconium fittings.

Using pump pressure, a solution of 100 kg of potassium hydrogen carbonate in aqueous solution and 41 kg of 5-(2-methylmercaptoethyl)-hydantoin in 400 l of water is fed hourly into a continuously operating pressurised column 8 made of special steel (compare FIG. 2) operated with steam. The reaction mixture is heated to 180° C. and has an average residence time of about 15 minutes at about 8 bar. Ammonia and carbon dioxide liberated is drawn off at the top of the reactor column by means of a pressure-maintaining valve. The reaction solution is depressurised at the bottom of the pressurised reactor and cooled with the heat exchanger 9. A quantity of 41.9 kg per hour of potassium methioninate in solution is obtained (94.5% of the theoretical).

Example 6

Figure 2:
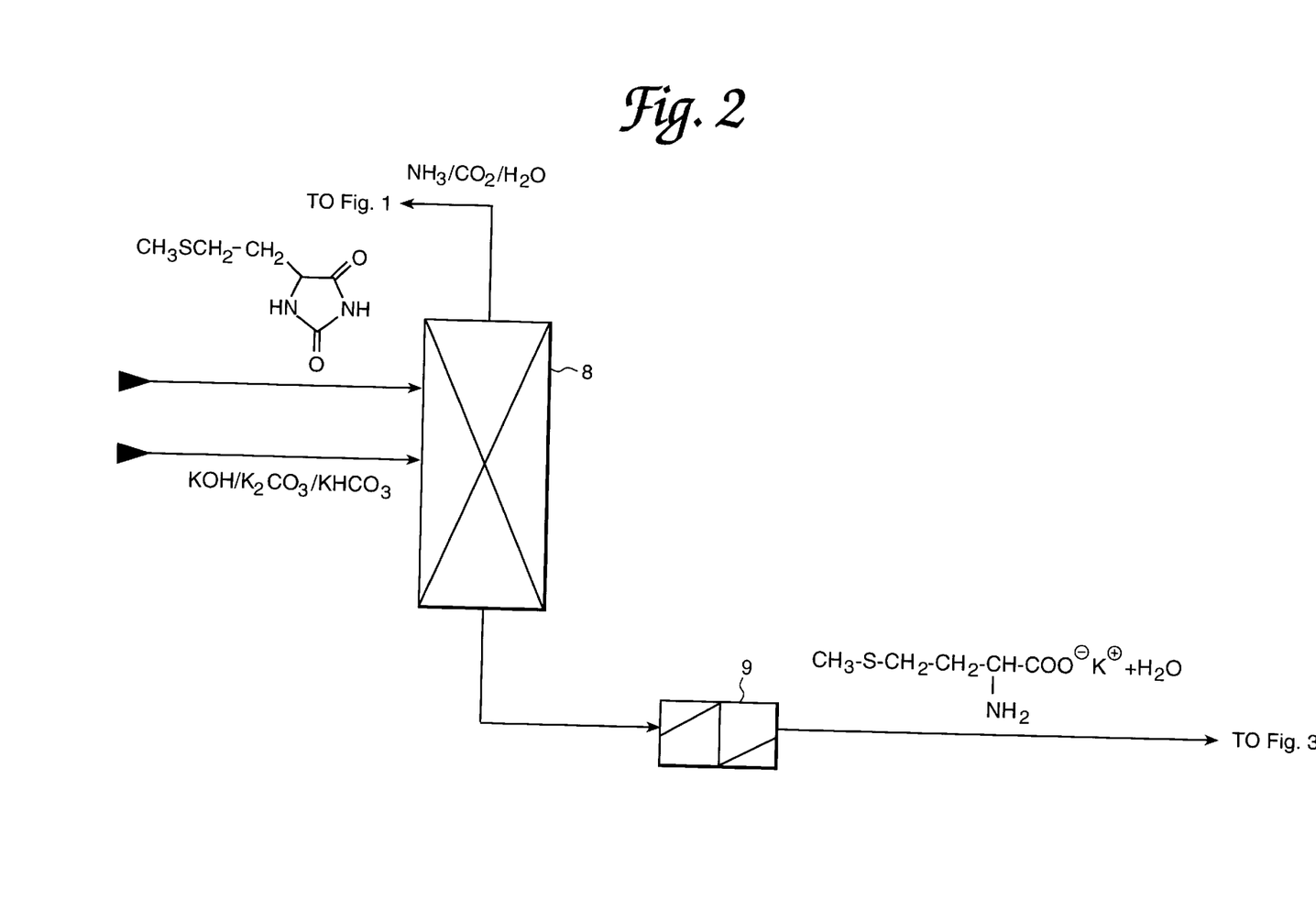
FIG. 2 shows a process sketch of the continuous hydrolysis of 5-(2-methylmercaptoethyl)-hydantoin to alkali metal methioninate.

An apparatus according to FIG. 2 is used, comprising a pressurised column having zirconium fittings.

Using a pump, 553 kg of 5-(2-methylmercaptoethyl)-hydantoin in 1600 l of reaction solution from hydantoin preparation according to FIG. 1 and 3550 l of a mixture of potassium carbonate/potassium hydrogen carbonate and potassium hydroxide in aqueous solution from mother liquor recycling after methionine solids separation with a potassium content of 140 g per litre and a residual methionine content of 120 g per litre are fed hourly into the top of a pressurised hydrolysis column 8 with zirconium fittings. The reaction temperature is 165° C.; the reaction pressure is 7 bar. The ammonia and carbon dioxide liberated are removed at the top of the column by means of a pressure-maintaining valve and fed to 5-(2-methylmercaptoethyl)-hydantoin synthesis again.

At the bottom of the pressure apparatus, 5150 l per hour of an aqueous mixture with 96.5 g of potassium per litre and 175 g of methionine per litre (corresponding to an increase of 476 kg/h methionine in the system as a whole) are obtained (yield: 100%). The reaction solution is cooled by means of a heat exchanger 9 and fed to methionine liberation.

Example 7

Figure 3:
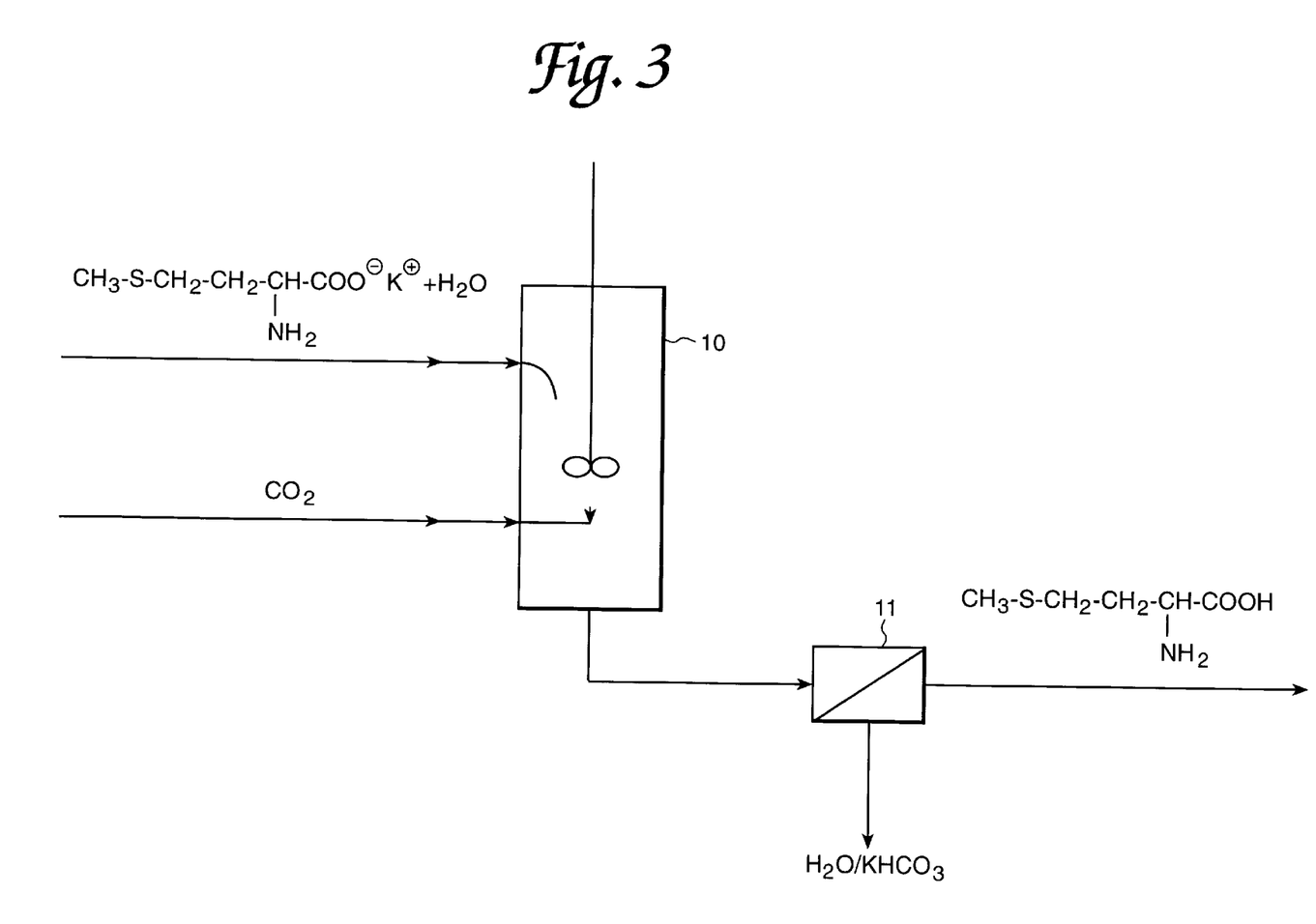
FIG. 3 shows a process sketch of the continuous liberation and isolation of D,L-methionine from alkali metal-D,L-methioninate.

Example of the liberation of D,L-methionine from potassium-D,L-methioninate (FIG. 3)

686 l per hour of an aqueous solution with 83.6 kg of potassium D,L-methioninate (hydrolysis solution of 5-(2-methylmercaptoethyl)-hydantoin) with additionally 39.77 kg of recycled methionine and potassium compounds are fed in continuously at the top of a stirred reactor 10 with a capacity of 340 l. At the same time, carbon dioxide is fed in at the bottom of the reactor so that a pressure of 2–3 bar is carried in the reactor. Similarly, 0.38 kg per hour of defoaming agent are fed into the reactor in the form of an aqueous emulsion; this quantity corresponds to approximately 3940 ppm of defoaming agent per kilogram of total methionine. The reaction temperature is kept at 25° C. In order to keep a constant level in the reactor, quantities of reaction solution corresponding to the inflow are removed from the lower part of the reactor. The suspension removed is filtered, 66.5 kg per hour of solid D,L-methionine (calculated as dry substance) being obtained, and the mother liquor with a residual content of 39.77 kg of D,L-methionine can be recycled to the hydantoin hydrolysis stage as saponification agent. The yield is quantitative.

What is claimed is:

1. A process for the preparation of methionine or a salt of methionine, said process comprising the steps of
   (i) reacting the components 3-methylmercaptopropionaldehyde, hydrogen cyanide, ammonia and carbon dioxide or precursors from which said components can be prepared, optionally in the presence of water, to obtain 5-(2-methylmercaptoethyl)-hydantoin; and
   (ii) reacting 5-(2-methylmercaptoethyl)-hydantoin to obtain methionine or the salt thereof;
   wherein
   step (i) is initiated by means of at least one premixture so that a first mixture is formed containing at least $5/10$ of the 3-methylmercaptopropionaldehyde and at least $1/10$ of the hydrogen cyanide component or corresponding quantities of the precursors from which said components can be prepared, and containing less than $5/10$ of one of the components ammonia, carbon dioxide or of the precursor from which ammonia or carbon dioxide can be prepared, and this first mixture is combined with the other component(s) or precursor(s) for the reactive conversion to 5-(2-methylmercaptoethyl)-hydantoin, wherein the latter component(s) may be premixed in one or more additional mixtures.

2. The process according to claim 1, wherein at least $5/10$ of the hydrogen cyanide component, or corresponding proportions of the precursor from which hydrogen cyanide can be prepared, is used in the first mixture.

3. The process according to claim 2, wherein at least $9/10$ of the hydrogen cyanide component, or corresponding proportions of the precursor from which hydrogen cyanide can be prepared, is used in the first mixture.

4. The process according to claim 3, wherein at least $99/100$ of the hydrogen cyanide component, or corresponding proportions of the compound from which hydrogen cyanide can be prepared, is used in the first mixture.

5. The process according to claim 1, wherein ammonia and carbon dioxide, or the precursors from which ammonia or carbon dioxide can be prepared, are each used in a proportion of less than $5/10$ of their use quantities in the first mixture.

6. The process according to claim 5, wherein ammonia and carbon dioxide, or the precursors from which ammonia or carbon dioxide can be prepared, are each used in a proportion of no more than $1/10$ of their use quantities in the first mixture.

7. The process according to claim 6, wherein ammonia and carbon dioxide, or the precursors from which ammonia or carbon dioxide can be prepared, are each used in a proportion of no more than $1/100$ of their use quantities in the first mixture.

8. The process according to claim 1, wherein no more than $5/10$ of the total quantity of water used is added in the first mixture.

9. The process according to claim 8, wherein no more than $1/10$ of the total quantity of water used is added in the first mixture.

10. The process according to claim 9, wherein no more than $1/100$ of the total quantity of water used is added in the first mixture.

11. The process according to claim 1, wherein no component is metered in afterwards.

12. The process according claim 1, wherein all the components are used in a total of two premixtures.

13. The process according to claim 1, wherein the premixture(s) and optionally individual components are introduced into a reaction mixture already obtained and containing 5-(2-methylmercaptoethyl)-hydantoin.

14. The process according to claim 13, wherein the premixture(s) and optionally individual components are fed into the reaction mixture either adjacently or at staggered or flow-dependent intervals of no more than 30 s.

15. The process according to claim 1, wherein the steps of the process are carried out at a temperature above 80° C.

16. The process according to claim 1 wherein the steps of the process are carried out at a pressure above 10 bar.

17. The process according to claim 1 which is carried out continuously.

18. A process for the continuous preparation of methionine or a salt of methionine comprising the steps of
(i) reacting the components 3-methylmercaptopropionaldehyde, hydrogen cyanide, ammonia and carbon dioxide or precursors from which said components can be prepared, optionally in the presence of water, to obtain 5-(2-methylmercaptoethyl)-hydantoin; and
(ii) reacting 5-(2-methylmercaptoethyl)-hydantoin to obtain methionine or the salt thereof;
wherein
the components and/or precursors of step (i) are introduced into a reaction mixture which is formed from said components and/or precursors and additionally contains at least $1/10$ of the quantity of 5-(2-methylmercaptoethyl)-hydantoin that can theoretically be formed;

and the process is carried out at a pressure of at least 3 bar.

19. The process according to claim 18 which is carried out at a temperature above 80° C.

20. The process according to claim 18 which is carried out at a pressure above 10 bar.

21. The process according to claim 18 wherein the reaction of the components and/or precursors is initiated by means of at least one premixture in such a way that a first mixture is formed containing at least $5/10$ of the 3-methylmercaptopropionaldehyde and at least $1/10$ of the hydrogen cyanide component or corresponding quantities of the precursors from which these components can be prepared, and less than $5/10$ of one of the components ammonia, carbon dioxide or of the precursors from which ammonia or carbon dioxide can be prepared, and wherein the first mixture is combined with the other component(s) and/or precursor(s) for the reactive conversion to 5-(2-methylmercaptoethyl)-hydantoin, wherein the latter component(s) may be premixed in one or more additional mixtures.

22. The process according to claim 18, wherein at least $5/10$ of the hydrogen cyanide component or corresponding proportions of the precursor from which hydrogen cyanide can be prepared, is used in the first mixture.

23. The process according to claim 22, wherein at least $9/10$ of the hydrogen cyanide component or corresponding proportions of the precursor from which hydrogen cyanide can be prepared, is used in the first mixture.

24. The process according to claim 23, wherein at least $99/100$ of the hydrogen cyanide component or corresponding proportions of the precursor from which hydrogen cyanide can be prepared, is used in the first mixture.

25. The process according to claim 22, wherein ammonia and carbon dioxide or the precursors from which ammonia or carbon dioxide can be prepared are each used in a proportion of less than $5/10$ of their use quantities in the first mixture.

26. The process according to claim 25, wherein ammonia and carbon dioxide or the precursors from which ammonia or carbon dioxide can be prepared are each used in a proportion of no more than $1/10$ of their use quantities in the first mixture.

27. The process according to claim 26, wherein ammonia and carbon dioxide or the precursors from which ammonia or carbon dioxide can be prepared are each used in a proportion of no more than $1/100$ of their use quantities in the first mixture.

28. The process according to claim 18, wherein no more than $5/10$ of the total quantity of water used is added in the first mixture.

29. The process according to claim 28, wherein no more than $1/10$ of the total quantity of water used is added in the first mixture.

30. The process according to claim 29, wherein at most $1/100$ of the total quantity of water used is added in the first mixture.

31. The process according to claim 18, wherein the components are fed into the reaction mixture immediately or with a flow-dependent pre-reaction time of at most 30 s.

* * * * *